United States Patent
Yoon

(10) Patent No.: US 6,875,227 B2
(45) Date of Patent: Apr. 5, 2005

(54) METAL STENT FOR INSERTION IN CORONARY ARTERY

(75) Inventor: Jung-Han Yoon, Hyundai Apt. 102-1303, Myungryun-dong, Kangwon, Wonju 220-040 (KR)

(73) Assignee: Jung-Han Yoon, Wonju (KR)

( * ) Notice: Subject to any disclaimer, the term of this patent is extended or adjusted under 35 U.S.C. 154(b) by 114 days.

(21) Appl. No.: 10/276,376
(22) PCT Filed: May 21, 2001
(86) PCT No.: PCT/KR01/00833
§ 371 (c)(1), (2), (4) Date: Nov. 15, 2002
(87) PCT Pub. No.: WO01/89417
PCT Pub. Date: Nov. 29, 2001

(65) Prior Publication Data
US 2003/0114921 A1 Jun. 19, 2003

(30) Foreign Application Priority Data
May 22, 2000 (KR) ........................................ 2000-27462

(51) Int. Cl.[7] .................................................. A61F 2/06
(52) U.S. Cl. ..................................... 623/1.16; 623/1.15
(58) Field of Search ................................ 623/1.12, 1.15, 623/1.16, 1.17, 1.18, 1.2, 1.22, 1.27, 1.35; 606/194, 195

(56) References Cited

U.S. PATENT DOCUMENTS

| 5,443,496 | A | | 8/1995 | Schwartz et al. ............... 623/1 |
| 5,735,871 | A | | 4/1998 | Sgro ........................... 606/198 |
| 6,013,854 | A | | 1/2000 | Moriuchi ...................... 623/11 |
| 6,416,543 | B1 | * | 7/2002 | Hilaire et al. ............... 623/1.16 |
| 6,440,162 | B1 | * | 8/2002 | Cox et al. .................. 623/1.15 |
| 6,508,834 | B1 | * | 1/2003 | Pinchasik et al. .......... 623/1.16 |
| 6,540,775 | B1 | * | 4/2003 | Fischell et al. ............ 623/1.15 |

* cited by examiner

Primary Examiner—Corrine McDermott
Assistant Examiner—Hieu Phan
(74) Attorney, Agent, or Firm—Fleshner & Kim, LLP

(57) ABSTRACT

The object of this invention is to provide a metal stent used for insertion into a coronary artery to treat a patient suffering from angina pectoris or myocardial infarction due to a coronary artery disease. This stent consists of a plurality of primary stent units (1), each having a zigzag shape rounded at its bent portions and being expandable in a circumferential direction. The primary stent units (1) are assembled into a single cylindrical structure of the stent such that each two primary stent units (1) are integrated into one secondary stent unit by a first strut (2') or (2") connecting each projected bent portion of each of the two primary stent units (1) to an associated bent portion of the other. Each two secondary stent units are integrated into a desired stent by a plurality of hook-shaped second struts (3) connecting the projected bent portions of the two secondary stent units to each other.

16 Claims, 4 Drawing Sheets

METAL STENT FOR INSERTION IN CORONARY ARTERY

TECHNICAL FIELD

The present invention relates, in general, to medical care instruments, or so-called "stents" for insertion in blood vessels and, more particularly, to a coronary care stent made of a metal inserted in the coronary artery to treat a patient suffering from angina pectoris or myocardial infarction due to a coronary artery disease.

BACKGROUND ART

Coronary artery disease is typically causes ischemia of the heart muscle by involving the coronary artery that is supplying the blood and nutrient to the heart muscle. The most typical etiological factor of such coronary artery diseases is arteriosclerosis. When plaque, formed by the mixing of cholesterol, other lipids, and a variety of components in the coronary artery and deposited on the inner lining of arterial walls, is excessively built up inside of the arterial lumen, the plaque undesirably causes an artery stenosis and ischemia of the heart muscle, thus making the heart muscle suffer lack of oxygen and nutritive substances. In the case of lack of oxygen and nutritive substance to the heart muscle due to ischemia of the heart muscle, a patient suffers angina pectoris or myocardial infarction, which may be fatal.

In the prior art, the non-surgical treatments of patients suffering from such coronary artery diseases use the two types of devices: an expandable balloon catheter or an expandable stent to enlarge the lumen and improve the angina, both being used for non-surgical insertion into a troubled coronary artery.

In the interventional treatment of a coronary artery disease using an expandable balloon, a guiding catheter is primarily inserted into the artery of the femoral region or the arm, and is secondarily positioned at the inlet of the coronary artery having the troubled lesion. In such a case, the term "lesion" means the focus or the narrowed or stenosed portion of the coronary artery due to built up plaque. After the guiding catheter positioning, a guide wire is navigated down into the coronary artery across the narrowed lesion site under the fluoroscopic guidance. Thereafter, a balloon-tipped catheter is inserted into the coronary artery over or along the guide wire until the catheter positioned at the lesion. The balloon is, thereafter, appropriately expanded to compress the plaque, and expands the narrowed or stenosed vessel to improve the perfusion in the heart muscle.

In case of the interventional treatment using a metallic stent, stent-mounted balloon catheter is inserted at the lesion of a troubled coronary artery after trials of balloon expansion and the balloon catheter with stent mounted is appropriately expanded and deployed at the lesion site. Therefore, the stent is permanently set in the lesion to expand the narrowed or stenosed vessel and allow a smooth circulation of blood in the coronary artery. The interventional treatment using such a stent is an effective treatment, as the stent maintains the expanded state of the vessel for a lengthy period of time. In comparison with the balloon catheter only, the treatment using such a stent reduces the possibility of recurrence of vessel narrowing. In addition, the stent buttresses the inner lining of the coronary arterial walls, and so the stent can be effective for treating a patient suffering from a complication after the procedure.

However, atherosclerotic arterial walls around the lesion are typically too rigid, so that they are apt to narrow or be constricted again due to an acute elastic recoil after an angioplasty Therefore, it is necessary for stents to sufficiently support the arterial wall in a radial direction and maintain the expanded state of the vessels for a desired lengthy period of time.

Another expected cause of the re-stenosis of the vessel after an angioplasty using an expandable stent is an excessive proliferation of a neo-intima within the stent. The stent is an in vivo foreign substance, and treatment with an insertion of a stent in the vessel inevitably causes morbid biological injury to the vessel. Therefore, intima is newly, inevitably produced within the vessel inside of the stent. Such a newly produced intima within the vessel is a so-called "neo-intima" in the description of this invention. Such a production of the neo-intima within the stent after an angioplasty using the stent is recognized as a normal healing response after injury. However, in the case of about 20~30% of patients of the angioplasty using the stents, the neo-intima within a stent is excessively produced to cause the re-narrowing of the stented artery.

In an effort to effectively overcome such a re-stenosis of vessels due to an excessive production of the neo-intima within the stent, it has been required in the art to propose and use a stent designed for effective application of various anti-proliferative agents, which should reduce the excessive production of the neo-intima after the angioplasty.

DISCLOSURE OF THE INVENTION

Accordingly, the present invention has been made keeping in mind the above problems occurring in the prior art, and an object of the present invention is to provide a coronary care stent, which is made of a metal and is used for deployment in the coronary artery to treat a patient suffering from angina pectoris or myocardial infarction due to a coronary artery disease, and which is reduced in its profile, in addition to having improved flexibility, improved side-branch accessibility, larger interstrut spaces, and enhanced radial support force, different from conventional stents, and which is desirably enlarged in its surface area to allow an effective application and preservation of a sufficient amount of anti-intimal proliferation agents to the inner lining of the arterial walls after an angioplasty using the stent, and which effectively transfers the agent(s) to the inner lining of the arterial wall around the lesion having the stent, and allows the topical agent(s) to remain in the vicinity of the lesion for a desired lengthy period of time.

In order to accomplish the above object, the present invention provides a metal stent used for insertion in a coronary artery, comprising: a plurality of primary stent units each having a zigzag shape, rounded at its bent portions and being expandable in a circumferential direction, the primary stent units being assembled into a single cylindrical structure of the stent such that each two primary stent units are integrated into one secondary stent unit by a first strut connecting each projected bent portion of each of the two primary stent units to an associated dented bent portion of the other, and each two secondary stent units are integrated into a desired stent by a plurality of hook-shaped second struts connecting the projected bent portions of the two secondary stent units to each other.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
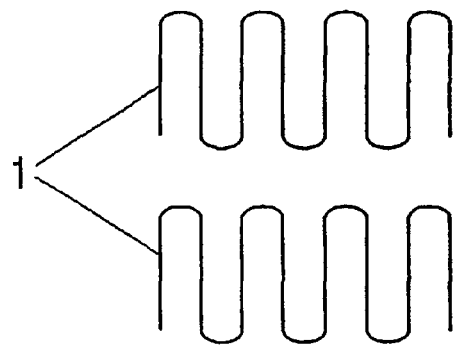
FIG. 1 is a view, showing two primary stent units, each having a modified zigzag shape, in accordance with the preferred embodiment of the present invention.

Reference now should be made to the drawings, in which the same reference numerals are used throughout the different drawings to designate the same or similar components.

Figure 2A:
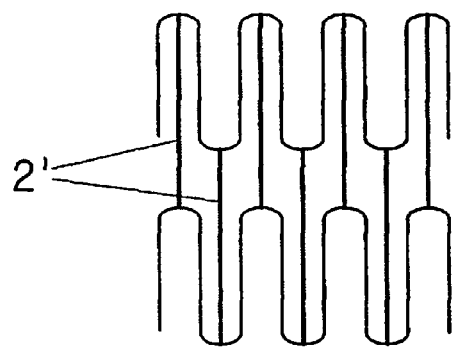
FIG. 2a is a view, showing a secondary stent unit formed by integrating the two primary units of FIG. 1 together into a single structure using a plurality of straight connecting struts in accordance with an embodiment of this invention.
Figure 2B:
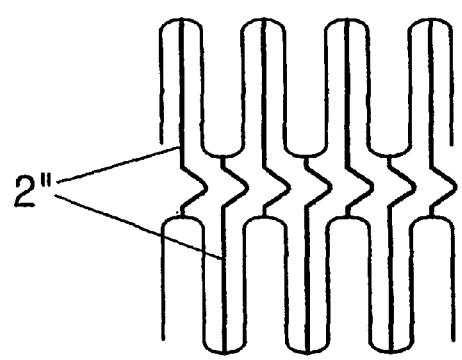
FIG. 2b is a view, showing a secondary stent unit formed by integrating the two primary units of FIG. 1 together into a single structure using a plurality of spoon-shaped connecting struts in accordance with another embodiment of this invention.

As shown in FIGS. 1, 2a and 2b, the coronary care stent of this invention comprises a plurality of primary stent units 1, each having a modified zigzag shape rounded at its bent portions and being expandable in a circumferential direction, and a plurality of first connecting struts used for integrating two primary units 1 together into a single structure to form a secondary stent unit.

In the coronary care stent of this invention, the modified zigzag structure of each primary stent unit 1 allows the unit 1 to be expandable in a circumferential direction when the stent is expanded. The primary stent units 1 thus enlarge the diameter of the stent in the case of an expansion of the stent. In the present invention, it is preferable to set the thickness of each primary stent unit 1 to 0.05 mm~0.07 mm.

In order to produce a desired stent using the primary stent units 1 of this invention, two primary stent units 1 having the same shape are parallely arranged prior to integrating the two primary units 1 together into a secondary stent unit using a plurality of first struts. In such a case, the first struts connect the projected bent portions of each of the two primary units 1 to the dented bent portions of the other. In the present invention, a plurality of straight struts 2' of FIG. 2a or a plurality of spoon-shaped struts 2" of FIG. 2b may be used as the first connecting struts used for forming a desired secondary stent unit by connecting two primary stent units 1. It is also preferable to set the thickness of each first connecting strut 2' or 2" to 0.05 mm~0.07 mm, and the width of each strut 2' or 2" to 0.05 mm~0.15 mm. In addition, the total length of each secondary stent unit is preferably set to 6 mm~7 mm.

Figure 3A:
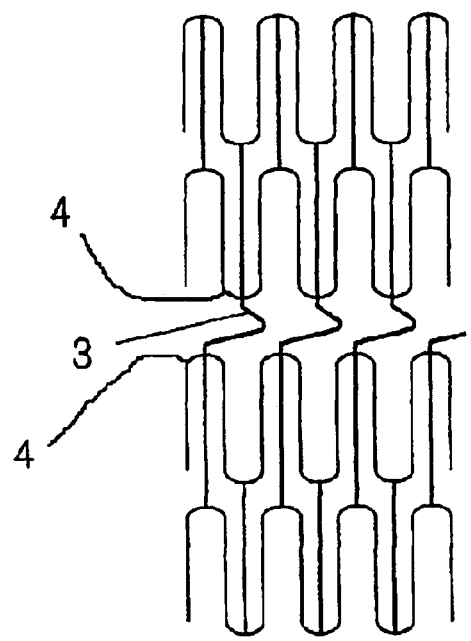
FIG. 3a is a view, showing a stent formed by integrating two secondary units of FIG. 2b together into a single structure using a plurality of hook-shaped connecting struts in accordance with an embodiment of this invention.
Figure 3B:
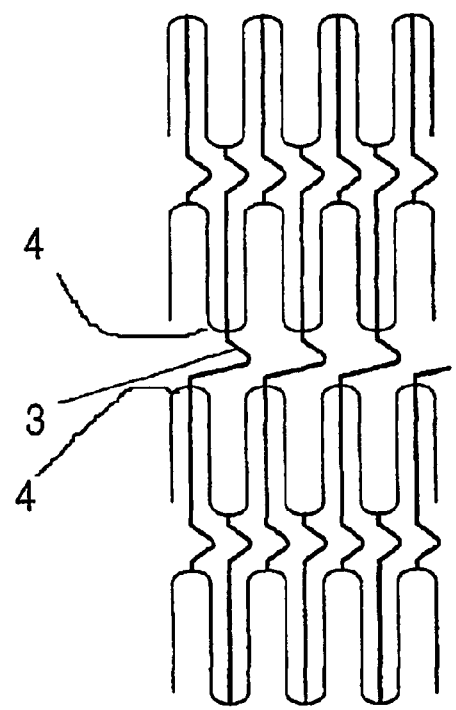
FIG. 3b is a view, showing a stent formed by integrating two secondary units of FIG. 2a together into a single structure using a plurality of hook-shaped connecting struts in accordance with another embodiment of this invention.

In order to allow the stent of this invention made of such secondary stent units to easily and smoothly reach a target lesion of a coronary artery, in addition to compensating for a reduction in the total length of the stent during an expansion of the stent within the coronary artery, two secondary stent units are integrated into a single structure using a plurality of second connecting struts 3 having a hook shape as shown in FIGS. 3a and 3b, thus forming a desired stent. In such a case, the hook-shaped second struts 3 connect the projected bent portions of the two secondary stent units to each other.

In order to improve the flexibility of a resulting stent, the hook-shaped second struts 3, used for connecting two secondary stent units to each other into a desired stent, preferably have a width of ⅔ of the width of the first struts 2' or 2" used for connecting the primary stent units 1 to each other into a secondary stent unit. It is also preferable to set the gap between two secondary stent units in a stent to 0.5 mm~1.0 mm.

Figure 4:
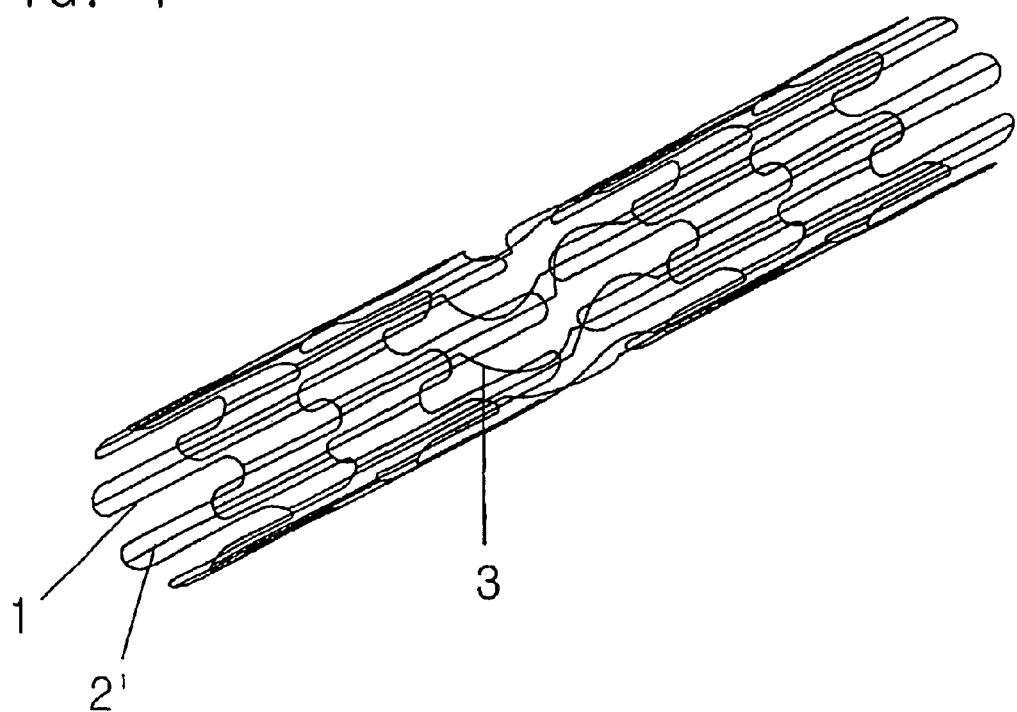
FIG. 4 is a perspective view of the expandable stent, consisting of a plurality of primary stent units of this invention integrated into a single structure using the straight connecting struts.
Figure 5:
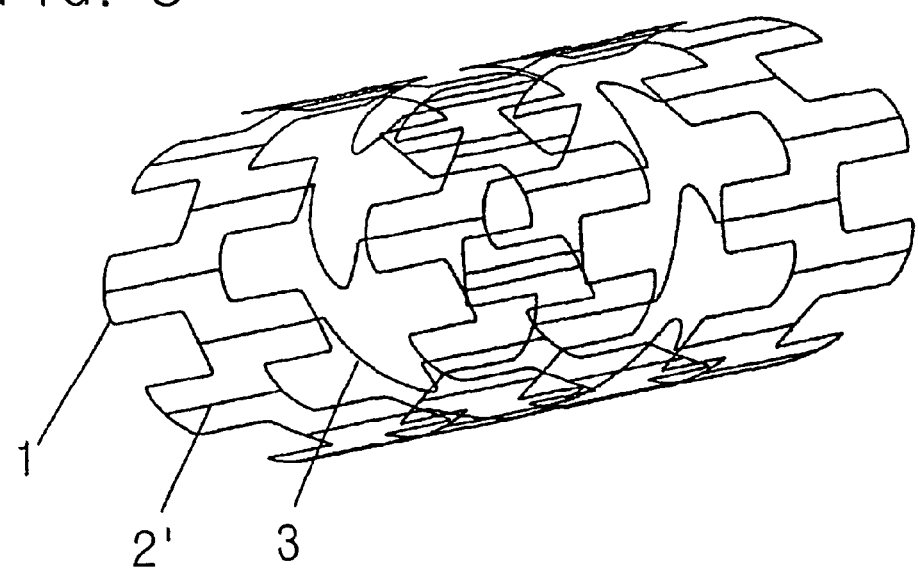
FIG. 5 is a perspective view of the stent of FIG. 4 when the stent is expanded to accomplish a desired diameter.

In the present invention, the cylindrical stent of this invention, having the above-mentioned structure as best seen in FIG. 4, is preferably made of stainless steel or shape-memory alloy through a laser cutting process. When the cylindrical stent is fully expanded through a balloon-added expansion process or a self-expansion process, the diameter of the expanded stent becomes 2.5 mm~5.0 mm. In such a case, the total length of the fully expanded stent becomes 6 mm~47 mm. The shape of the fully expanded stent is shown in FIG. 5.

Figure 6A:
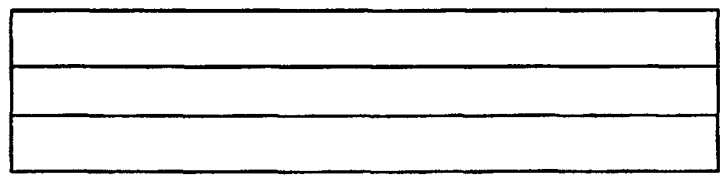
FIG. 6a is a plan view of a connecting strut having a continuous axial groove formed along the central axis of the surface of the strut in accordance with an embodiment of the present invention.
Figure 6B:
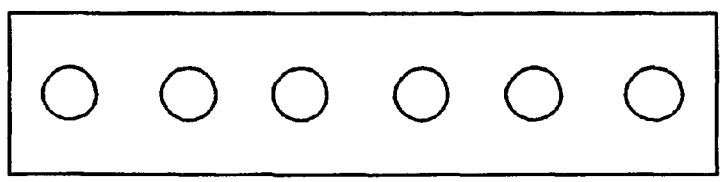
FIG. 6b is a plan view of a connecting strut having a plurality of grooves or holes formed along the surface of the strut in accordance with another embodiment of the present invention.

In order to more effectively inhibit an excessive, proliferation of a neo-intima within the stent after an angioplasty, it is necessary for the coronary care stent to allow an effective application of a sufficient amount of anti-intimal proliferation agents to the inner lining of the coronary artery at a position around the stent, and for the applied agents to remain around the stent for a desired lengthy period of time. Known examples of such anti-intimal proliferation agents, capable of inhibiting an excessive proliferation of the neo-intima after an angioplasty, are anti-cytokinetic agents, such as Paclitaxel, antiplatelet agents, such as Cilostazol, anti-inflammatory agents, and anticoagulant agents. In addition, it is preferable to form the coronary care stent to have a thin sidewall, of which the thickness does not exceed a predetermined level. In order to accomplish the above objects, it is preferable to design the first and second struts for the primary and secondary stent units such that the struts each have a hole or a U-shaped cross-sectioned groove. In the present invention, when it is desired to form the groove or hole in a continuous profile, it is preferable to form a U-shaped cross-sectioned continuous axial groove along the central axis of the strut's surface through a laser cutting process as shown in FIG. 6a On the other hand, when it is desired to form the groove or hole in a discontinuous profile, it is preferable to form a plurality of holes or a plurality of U-shaped cross-sectioned grooves along the central axis of the strut's surface through a laser cutting process as shown in FIG. 6b. That is, the desired cross-section of the first and second struts may be formed by a continuous axial groove, or a plurality of discontinuous grooves or holes on the strut's surface as desired. In the present invention, the arrangement of the discontinuous grooves or holes on the strut's surface is not limited to the embodiment of FIG. 6b, but may be somewhat freely changed as desired without affecting the functioning of this invention. For example, the discontinuous grooves or holes may be arranged on the strut's surface in a straight arrangement or a zigzag arrangement. In the present invention, it is preferable to set the depth of the continuous groove or the discontinuous grooves of the strut to 0.02 mm~0.04 mm, and the width to 0.03 mm~0.05 mm.

Since the first and second struts included in the coronary care stent of this invention have the above-mentioned grooves or holes forming a desired cross-section of each strut, a polymer-based anti-intimal proliferation agent mixture is effectively applied to and more reliably retained by the struts for a desired lengthy period of time without increasing the thickness of the cylindrical stent's sidewall, different from conventional stents.

INDUSTRIAL APPLICABILITY

As described above, the present invention provides a coronary care stent, which is made of a metal and is used for insertion into the coronary artery to treat a patient suffering from angina pectoris or myocardial infarction due to a coronary artery disease. The stent of this invention is specifically designed such that it has sufficient radial support force capable of effectively maintaining the expanded state of the vessel after an angioplasty, different from conventional stents. The stent is also reduced in its thickness, in addition to having improved flexibility, improved sidebranch accessibility, and larger interstrut spaces. This stent is desirably enlarged in its surface area to allow an effective application and retention of a sufficient amount of antiintimal proliferation agents after an angioplasty using the stent for a desired lengthy period of time. That is, the connecting struts included in the coronary care stent of this invention have continuous or discontinuous grooves or holes forming a desired cross-section of each strut, and so a polymer-based anti-intimal proliferation agent mixture is effectively applied to and reliably retained by the struts for a desired lengthy period of time without increasing the profile of the cylindrical stent. Therefore, the stent of this invention effectively prevents the vessel from being narrowed or constricted again after an angioplasty using the stent, in addition to inhibiting a proliferation of neo-intima within the vessel having the stent, different from the conventional stents.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A metal stent for insertion in a coronary artery, comprising:

a plurality of primary stent units each having a zigzag shape rounded at its bent portions and being expandable in a circumferential direction, said primary stent units being assembled into a single cylindrical structure of the stent such that each two primary stent units are integrated into one secondary stent unit by a first strut connecting each projected bent portion of each of the two primary stent units to an associated dented bent portion of the other, and each two secondary stent units are integrated into a desired stent by a plurality of hook-shaped second struts connecting the projected bent portions of the two secondary stent units to each other, each of said first and second struts having a hole on its surface.

2. The metal stent according to claim 1, wherein said first strut connecting the primary stent units to each other is a straight strut.

3. The metal stent according to claim 1, wherein said first strut connecting the primary stent units to each other is a spoon-shaped strut.

4. The metal stent according to claim 1, wherein said first stent connecting the primary stent units to each other has a thickness of 0.05 mm~0.07 mm, and a width of 0.05 mm~0.15 mm.

5. The metal stent according to claim 1, wherein each of the secondary stent units has a total length of 6 mm~7 mm.

6. The metal stent according to claim 1, wherein each of said hook-shaped second struts connecting the two secondary stent units to each other has a width of ⅔ of a width of said first strut.

7. The metal stent according to claim 1, wherein the two secondary stent units are arranged with a gap of 0.5 mm~1.0 mm between them.

8. The metal stent according to claim 1, wherein the stent is expandable through a balloon-added expansion process or a self-expansion process.

9. The metal stent according to claim 1, wherein the stent has a diameter of 2.5 mm~5.0 mm and a total length of 7 mm~39 mm when it is fully expanded.

10. The metal stent according to claim 1, wherein each of said first and second struts has a U-shaped cross-sectioned groove on its surface.

11. The metal stent according to claim 10, wherein said U-shaped cross-sectioned groove is a continuous groove.

12. The metal stent according to claim 11, wherein said groove has a depth of 0.02 mm~0.04 mm and a width of 0.03 mm~0.05 mm.

13. The metal stent according to claim 10, wherein said U-shaped cross-sectioned groove is a discontinuous groove.

14. The metal stent according to claim 1, wherein said hole is a discontinuous hole.

15. The metal stent according to claim 1, wherein said groove has a depth of 0.02 mm~0.04 mm and a width of 0.03 mm~0.05 mm.

16. The metal stent according to claim 1, wherein the stent is made of a stainless steel or a shape-memory alloy.

* * * * *